US007189823B2

(12) United States Patent
Bauer et al.

(10) Patent No.: US 7,189,823 B2
(45) Date of Patent: Mar. 13, 2007

(54) ANTIBODY AGAINST ILLFDYFNR

(75) Inventors: Anthony J. Bauer, Pittsburgh, PA (US); Gisela Bruenagel, Pittsburgh, PA (US); Robert H. Getzenberg, Lutherville, MD (US); Robert E. Schoen, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 11/133,177

(22) Filed: May 20, 2005

(65) Prior Publication Data
US 2005/0221372 A1    Oct. 6, 2005

Related U.S. Application Data

(63) Continuation of application No. 10/350,367, filed on Jan. 24, 2003, now abandoned.

(60) Provisional application No. 60/412,612, filed on Sep. 19, 2002, provisional application No. 60/351,819, filed on Jan. 25, 2002.

(51) Int. Cl.
 *C07K 16/18* (2006.01)
(52) U.S. Cl. ............... 530/387.9; 530/388.26; 530/388.8; 530/328; 530/350
(58) Field of Classification Search ............ 530/387.9, 530/300, 350, 388.26, 388.8, 328
See application file for complete search history.

(56) References Cited

U.S. PATENT DOCUMENTS

| 4,161,519 A | 7/1979 | Talwar |
| 4,608,251 A | 8/1986 | Mia |
| 5,547,928 A | 8/1996 | Wu et al. |
| RE35,747 E | 3/1998 | Penman et al. |
| 5,824,490 A | 10/1998 | Coffey et al. |
| 5,830,677 A | 11/1998 | Wu et al. |
| 5,989,826 A | 11/1999 | Beausang et al. |
| 6,162,608 A | 12/2000 | Beausang et al. |
| 6,210,892 B1 | 4/2001 | Bennett et al. |
| 6,410,247 B1 | 6/2002 | Beausang et al. |

FOREIGN PATENT DOCUMENTS

| WO | WO 99/62942 | 12/1999 |
| WO | WO 00/65069 | 11/2000 |

OTHER PUBLICATIONS

Balasubramani et al. (Cancer Res. Jan. 2006; 66 (2): 763-769).*
Sistermans et al. (Cell Tissue Res. 1995; 280; 435-446).*
Holmes (Expert Opinion on Investigational Drugs. 2001; 10; 511-519).*
Brünagel et al., "Nuclear Matrix Protein Alterations Associated with Colon Cancer Metastasis to the Liver," *Clinical Cancer Research*, Oct. 2002, pp. 3039-3045, vol. 8.
Coffey, "Nuclear Matrix Proteins as Proteomic Markers of Preneoplastic and Cancer Lesions," Commentary re: G. Brunagel et al., Nuclear Matrix Protein Alterations Associated with Colon Cancer Metastasis to the Liver. Clin. Cancer Res., 8:3039-3045, 2002, *Clinical Cancer Research*, Oct. 2002, pp. 3031-3033, vol. 8.
Ahlquist, "Fecal Occult Blood Testing for Colorectal Cancer," *Gastroenterology Clinics of North America*, Mar. 1997, pp. 41-55, vol. 26, No. 1, W.B. Saunders Company.
Berezney et al., "Identification of a Nuclear Protein Matrix," *Biochemical and Biophysical Research Communications*, Oct. 23, 1974, pp. 1410-1417, vol. 60, No. 4, Academic Press, Inc.
Boyd et al., "Preneoplastic Alterations in Nuclear Morphology That Accompany Loss of Tumor Suppressor Phenotype," *Journal of the National Cancer Institute*, Jun. 19, 1991, pp. 862-866, vol. 83, No. 12.
Brünagel et al., "Identification of Nuclear Matrix Protein Alterations Associated with Human Colon Cancer," *Cancer Research*, Apr. 15, 2002, pp. 2437-2442, vol. 62, No. 8, American Association for Cancer Research.
Carriquiry et al., "Should Carcinoembryhonic Antigen be Used in the Management of Patients with Colorectal Cancer," *Diseases of the Colon Rectum*, Jul. 1999, pp. 921-929, vol. 42, No. 7, Lippincott Williams & Wilkins.
Cupo, "Electrophoretic analysis of nuclear matrix proteins and the potential clinical applications," *Journal of Chromatography*, Sep. 13, 1991, pp. 389-406, vol. 569, Nos. 1 & 2, Elsevier Science Publishers B.V., Amsterdam.
Douillard et al., "Monoclonal Antibodies Specific Immunotherapy of Gastrointestinal Tumors," *Hybridoma*, 1986, pp. S139-S149, vol. 5, Supp. 1, Mary Ann Liebert, Inc., New York.
Fey et al., "Nuclear matrix proteins reflect cell type of origin in cultured human cells," *Proc. Natl. Acad. Sci. USA*, Jan. 1988, pp. 121-125, vol. 85, Cell Biology.
Fey et al., "The Nuclear Matrix: Defining Structural and Functional Roles," *Critical Reviews in Eukaryotic Gene Expression*, 1991, pp. 127-143, vol. 1, Issue 2, CRC Press, Inc.
Geenen et al., "Major Complications of Coloscopy: Bleeding and Perforation," *Digestive Diseases*, Mar. 1975, pp. 231-235, vol. 20, No. 3.
Getzenberg et al., "Bladder Cancer-associated Nuclear Matrix Proteins," *Cancer Research*, Apr. 1, 1996, pp. 1690-1694, vol. 56, No. 7.
Getzenberg et al., "Identification of Nuclear Matrix Proteins in the Cancer and Normal Rat Prostate," *Cancer Research*, Dec. 15, 1991, pp. 6514-6520, vol. 51, No. 24.
Getzenberg et al., "Nuclear Matrix and the Regulation of Gene Expression: Tissue Specificity," *Journal of Cellular Biochemistry*, May 1994, pp. 22-31, vol. 55, No. 1, Wiley-Liss, Inc.
Getzenberg et al., "The Tissue Matrix: Cell Dynamics and Hormone Action," *Endocrine Reviews*, Aug. 1990, pp. 399-417, vol. 11, No. 3, The Endocrine Society, USA.

(Continued)

*Primary Examiner*—Stephen L. Rawlings
(74) *Attorney, Agent, or Firm*—Foley & Lardner LLP

(57) ABSTRACT

Proteins useful in the diagnosis of proliferative disorders of the colon are present in nuclear matrix protein preparations and can be characterized by molecular weight, isoelectric point, and amino acid sequence. The proteins may be identified, for example, by 2D-gel electrophoresis or by specific binding partners, such as antibodies.

1 Claim, No Drawings

OTHER PUBLICATIONS

Gevaert et al., "New Strategies in High Sensitivity Characterization of Proteins Separated from 1-D or 2-D Gels," *Methods in Protein Structure Analysis*, 1995, pp. 15-25, Plenum Press, New York, USA.

Godreau, "Office-Based Colonoscopy in a Family Practice," *Family Practice Research Journal*, Sep. 1992, pp. 313-321, vol. 12, No. 3, Human Sciences Press, Inc., New York.

Goeddel, "Systems for Heterologous Gene Expression," *Methods in Enzymology*, 1990, pp. 3-7, vol. 185, Academic Pres, Inc.

Goldenberg et al., "Carcinoembryonic Antigen in Histopathology: Immunoperoxidase Staining of Conventional Tissue Sections," *J. Natl. Cancer Inst.*, Jul. 1976, pp. 11-22, vol. 57, No. 1.

Greenlee et al., "Cancer Statistics, 2000," *A Cancer Journal for Clinicians*, Jan./Feb. 2000, pp. 7-33, vol. 50, No. 1, American Cancer Society.

Harlow et al. (Eds.), *Antibodies: A Laboratory Manual*, 1988, Cold Spring Harbor Laboratory.

Hermanson (Ed.), *Bioconjugate Techniques*, 1996, (Table of Contents Only), Academic Press, Inc., San Diego, CA.

Herrera et al., "Carcinoembryonic Antigen (CEA) as a Prognostic and Monitoring Test in Clinically Complete Resection of Colorectal Carcinoma," *Annals of Surgery*, Jan. 1976, pp. 5-9, vol. 183, No. 1, J.B. Lippincott Company.

Huston et al., "Protein engineering of antibody binding sites: Recovery of specific activity in an anti-digoxin single-chain Fv analogue produced in *Escherichia coli*," *Proc. Natl. Acad. Sci. USA*, Aug. 1998, pp. 5879-5883, vol. 85.

Kabat et al. (Eds), *Sequences of Proteins of Immunological Interest*, $4^{th}$ Edition, 1987 (Table of Contents Only), U.S. Department of Health and Human Services.

Keesee et al., "Nuclear matrix proteins in human colon cancer," *Proc. Natl. Acad. Sci. USA*, Mar. 1994, pp. 1913-1916, vol. 91.

Keesee et al., "Utilization of Nuclear Matrix Proteins for Cancer Diagnosis," *Critical Reviews in Eukaryotic Gene Expression*, 1996, pp. 189-214, vol. 6, Issues 2 & 3, Begell House, Inc.

Konety et al., "Identification of Nuclear Matrix Protein Alterations Associated with Renal Cell Carcinoma," *The Journal of Urology*, Apr. 1998, pp. 1359-1363, vol. 159, No. 4, American Urological Association, Inc.

Martell et al., "OVX1 and CEA in patients with colon carcinoma, colon polyps and benign colon disorders," *The International Journal of Biological Markers*, Jul.-Sep. 1998, pp. 145-149, vol. 13, No. 3, Wichtig Editore—Milano, Italy.

Merrifield, "Solid Phase Peptide Synthesis. I. The Synthesis of a Tetrapeptide," *J. Am. Chem. Soc.*, Jul. 20, 1963, pp. 2149-2154, vol. 85.

Miller et al., "Detection of Nuclear Matrix Proteins in Serum from Cancer Patients," *Cancer Research*, Jan. 15, 1992, pp. 422-427, vol. 52, No. 2.

Moertel et al., "An Evaluation of the Carcinoembryonic Antigen (CEA) Test for Monitoring Patients With Resected Colon Cancer," *JAMA*, Aug. 25, 1993, pp. 943-947, vol. 270, No. 8.

Patton et al., "Development of a Dedicated Two-Dimensional Gel Electrophoresis System that Provides Optimal Pattern Reproducibility and Polypeptide Resolution," *BioTechniques*, May 1990, pp. 518-527, vol. 8, No. 5.

Replogle-Schwab et al., "The Utilization of Nuclear Matrix Proteins for Cancer Diagnosis," *Critical Reviews in Eukaryotic Gene Expression*, 1996, pp. 103-113, vol. 6, Issues 2 & 3, Begell House, Inc.

Reynoso et al., "Carcinoembryonic Antigen in Patients with Different Cancers," *JAMA*, Apr. 17, 1972, pp. 361-365, vol. 200, No. 3.

Stewart et al. (Eds.), "Chapter 2, Laboratory Techniques in Solid Phase Peptide Synthesis," *Solid Phase Peptide Synthesis*, 1969, pp. 27-64, W.H. Freeman and Company.

Uhlén et al., "Gene Fusions for Purpose of Expression: An Introduction," *Methods in Enzymology*, 1990, pp. 129-143, vol. 185, Academic Press, Inc.

Wanebo et al., "Preoperative Carcinoembryonic Antigen Level as a Prognostic Indicator in Colorectal Cancer," *The New England Journal of Medicine*, Aug. 31, 1978, pp. 448-451, vol. 299, No. 9, Massachusetts Medical Society.

Weidner et al., "Localization of Nuclear Matrix Proteins (NMPs) in Multiple Tissue Types with NM-200.4™ (An Antibody Strongly Reactive with NMPs Found in Breast Carcinoma)," *American Journal of Pathology*, Jun. 1991, pp. 1293-1298, vol. 138, No. 6, American Association of Pathologists.

Wray et al., "Silver Staining of Proteins in Polyacrylamide Gels," *Analytical Biochemistry*, Nov. 15, 1981, pp. 197-203, vol. 118, No. 1, Academic Press.

Database SWISS PROTEIN 41, Accession Nos. P04090, Q99936, Q9UCX3, Q9UQ12. Nov. 1, 1986.

Database SWISS PROTEIN 41, Accession Nos. Q9UN16. Oct. 16, 2001.

Database SWISS PROTEIN 41, Accession No. Q9UL58. Oct. 16, 2001.

Database SWISS PROTEIN 41, Accession Nos. P80365, Q13194, Q8N439, Q96AN8. Sep. 15, 2003.

* cited by examiner

```
                       SEQUENCE LISTING

<160> NUMBER OF SEQ ID NOS: 36

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: (2)
<223> OTHER INFORMATION: variable amino acid

<400> SEQUENCE: 1

Pro Xaa Val Lys Phe Asn Ser Tyr Val Asp Gly Val Glu Val
  1               5                  10

<210> SEQ ID NO 2
<211> LENGTH: 8
<212> TYPE: PRT
<213> ORGANISM: Homo sapiens

<400> SEQUENCE: 2

Glu Gly Asp Leu Ile Glu Asp Tyr
  1               5

<210> SEQ ID NO 3
<211> LENGTH: 7
<212> TYPE: PRT
<213> ORGANISM: Homo sapiens

<400> SEQUENCE: 3

Tyr Pro Val Glu Ala Phe Asn
```

-continued

```
                    1               5

<210> SEQ ID NO 4
<211> LENGTH: 11
<212> TYPE: PRT
<213> ORGANISM: Homo sapiens

<400> SEQUENCE: 4

Thr Val Ala Pro Leu Phe Ile Val Ile Pro Asn
  1               5                  10

<210> SEQ ID NO 5
<211> LENGTH: 18
<212> TYPE: PRT
<213> ORGANISM: Homo sapiens
<220> FEATURE:
<221> NAME/KEY: MOD_RES
<222> LOCATION: (1)
<223> OTHER INFORMATION: variable amino acid

<400> SEQUENCE: 5

Xaa Val Thr Gly Leu Thr Gln Ile Glu Thr Leu Phe Ala Ala Pro Gly
  1               5                  10                  15

Val Asp

<210> SEQ ID NO 6
<211> LENGTH: 23
<212> TYPE: PRT
<213> ORGANISM: Homo sapiens

<400> SEQUENCE: 6

Ser Met Thr Glu Ala Glu Gln Gln Gln Leu Ile Asp Asp His Phe Leu
  1               5                  10                  15

Phe Asp Lys Pro Val Ser Pro
                 20

<210> SEQ ID NO 7
<211> LENGTH: 14
<212> TYPE: PRT
<213> ORGANISM: Homo sapiens

<400> SEQUENCE: 7

Ser Leu Pro Gln Asn Ile Pro Pro Leu Thr Gln Thr Pro Val
  1               5                  10

<210> SEQ ID NO 8
<211> LENGTH: 11
<212> TYPE: PRT
<213> ORGANISM: Homo sapiens

<400> SEQUENCE: 8

Val Leu Pro Gly Glu Ile Val Glu Tyr Ser Arg
  1               5                  10

<210> SEQ ID NO 9
<211> LENGTH: 20
<212> TYPE: PRT
<213> ORGANISM: Homo sapiens

<400> SEQUENCE: 9

Tyr Thr Ile Phe Asp Asn Phe Leu Ile Thr Asn Asp Glu Ala Tyr Ala
  1               5                  10                  15

Glu Glu Phe Gly
                 20
```

```
<210> SEQ ID NO 10
<211> LENGTH: 15
<212> TYPE: PRT
<213> ORGANISM: Homo sapiens
<220> FEATURE:
<221> NAME/KEY: MOD_RES
<222> LOCATION: (11)
<223> OTHER INFORMATION: variable amino acid

<400> SEQUENCE: 10

Gln Ile Asp Asn Pro Asp Tyr Lys Gly Thr Xaa Ile His Pro Glu
 1               5                  10                  15

<210> SEQ ID NO 11
<211> LENGTH: 15
<212> TYPE: PRT
<213> ORGANISM: Homo sapiens

<400> SEQUENCE: 11

Pro Ala Val Tyr Phe Lys Glu Gln Phe Leu Asp Gly Asp Gly Trp
 1               5                  10                  15

<210> SEQ ID NO 12
<211> LENGTH: 13
<212> TYPE: PRT
<213> ORGANISM: Homo sapiens

<400> SEQUENCE: 12

Thr Leu Ile Val Arg Pro Asp Asn Thr Tyr Glu Val Lys
 1               5                  10

<210> SEQ ID NO 13
<211> LENGTH: 11
<212> TYPE: PRT
<213> ORGANISM: Homo sapiens

<400> SEQUENCE: 13

Tyr Ala Val Leu Ile Thr Val Leu Gln Asp Ser
 1               5                  10

<210> SEQ ID NO 14
<211> LENGTH: 5
<212> TYPE: PRT
<213> ORGANISM: Homo sapiens

<400> SEQUENCE: 14

Asn Leu Pro Gln Glu
 1               5

<210> SEQ ID NO 15
<211> LENGTH: 11
<212> TYPE: PRT
<213> ORGANISM: Homo sapiens

<400> SEQUENCE: 15

Thr Glu Pro Glu Leu Gln Asp Lys Ile His Gln
 1               5                  10

<210> SEQ ID NO 16
<211> LENGTH: 12
<212> TYPE: PRT
<213> ORGANISM: Homo sapiens

<400> SEQUENCE: 16
```

Thr Asp Ala Pro Ser Phe Ser Asp Ile Pro Asn Leu
1               5                   10

<210> SEQ ID NO 17
<211> LENGTH: 9
<212> TYPE: PRT
<213> ORGANISM: Homo sapiens
<220> FEATURE:
<221> NAME/KEY: MOD_RES
<222> LOCATION: (1)
<223> OTHER INFORMATION: variable amino acid

<400> SEQUENCE: 17

Xaa Gln Lys Glu Asp Val Pro Ser Glu
1               5

<210> SEQ ID NO 18
<211> LENGTH: 8
<212> TYPE: PRT
<213> ORGANISM: Homo sapiens

<400> SEQUENCE: 18

Asn Ala Phe Asn Asp Gly Leu Lys
1               5

<210> SEQ ID NO 19
<211> LENGTH: 17
<212> TYPE: PRT
<213> ORGANISM: Homo sapiens

<400> SEQUENCE: 19

Tyr Phe Asp Ser Phe Gly Asp Leu Ser Ser Ala Ser Ala Ile Met Gly
1               5                   10                  15

Asn

<210> SEQ ID NO 20
<211> LENGTH: 16
<212> TYPE: PRT
<213> ORGANISM: Homo sapiens

<400> SEQUENCE: 20

Thr Tyr Phe Ser His Ile Asp Val Ser Pro Gly Ser Ala Gln Val Lys
1               5                   10                  15

<210> SEQ ID NO 21
<211> LENGTH: 9
<212> TYPE: PRT
<213> ORGANISM: Homo sapiens

<400> SEQUENCE: 21

Ser Leu Asp Glu Gln Glu Gln Thr Lys
1               5

<210> SEQ ID NO 22
<211> LENGTH: 11
<212> TYPE: PRT
<213> ORGANISM: Homo sapiens

<400> SEQUENCE: 22

Ala Lys Thr Asp Phe Ala Thr Phe Leu Tyr Thr
1               5                   10

<210> SEQ ID NO 23
<211> LENGTH: 10
<212> TYPE: PRT

```
<213> ORGANISM: Homo sapiens

<400> SEQUENCE: 23

Leu Lys Tyr Glu Asn Glu Val Ala Leu Arg
 1               5                  10

<210> SEQ ID NO 24
<211> LENGTH: 9
<212> TYPE: PRT
<213> ORGANISM: Homo sapiens

<400> SEQUENCE: 24

Val Tyr Leu Glu Pro Leu Val Phe Arg
 1               5

<210> SEQ ID NO 25
<211> LENGTH: 10
<212> TYPE: PRT
<213> ORGANISM: Homo sapiens

<400> SEQUENCE: 25

Arg Ala Pro Phe Gln Glu Leu Tyr Asn Asp
 1               5                  10

<210> SEQ ID NO 26
<211> LENGTH: 14
<212> TYPE: PRT
<213> ORGANISM: Homo sapiens
<220> FEATURE:
<221> NAME/KEY: MOD_RES
<222> LOCATION: (1)
<223> OTHER INFORMATION: variable amino acid
<220> FEATURE:
<221> NAME/KEY: MOD_RES
<222> LOCATION: (13)
<223> OTHER INFORMATION: variable amino acid

<400> SEQUENCE: 26

Xaa Phe Tyr Gln Leu Asp Ala Tyr Pro Ser Gly Ala Xaa Tyr
 1               5                  10

<210> SEQ ID NO 27
<211> LENGTH: 7
<212> TYPE: PRT
<213> ORGANISM: Homo sapiens

<400> SEQUENCE: 27

Val Ile Glu Ala Phe Asn Arg
 1               5

<210> SEQ ID NO 28
<211> LENGTH: 9
<212> TYPE: PRT
<213> ORGANISM: Homo sapiens

<400> SEQUENCE: 28

Ile Leu Leu Phe Asp Tyr Phe Asn Arg
 1               5

<210> SEQ ID NO 29
<211> LENGTH: 9
<212> TYPE: PRT
<213> ORGANISM: Homo sapiens

<400> SEQUENCE: 29

Val Leu Val Ala Leu Glu Pro Leu Ser
```

<210> SEQ ID NO 30
<211> LENGTH: 17
<212> TYPE: PRT
<213> ORGANISM: Homo sapiens

<400> SEQUENCE: 30

Gln Phe Tyr Gln Leu Asp Ala Tyr Pro Ser Gly Ala Trp Tyr Tyr Val
1               5                   10                  15
Pro

<210> SEQ ID NO 31
<211> LENGTH: 10
<212> TYPE: PRT
<213> ORGANISM: Homo sapiens

<400> SEQUENCE: 31

Phe Phe Val Ala Leu Phe Pro Glu Val Phe
1               5                   10

<210> SEQ ID NO 32
<211> LENGTH: 17
<212> TYPE: PRT
<213> ORGANISM: Homo sapiens

<400> SEQUENCE: 32

Gln Phe Tyr Gln Leu Asp Ala Tyr Pro Ser Gly Ala Trp Tyr Tyr Val
1               5                   10                  15
Pro

<210> SEQ ID NO 33
<211> LENGTH: 12
<212> TYPE: PRT
<213> ORGANISM: Homo sapiens

<400> SEQUENCE: 33

Thr Asp Ala Pro Ser Phe Ser Asp Ile Pro Asn Leu
1               5                   10

<210> SEQ ID NO 34
<211> LENGTH: 12
<212> TYPE: PRT
<213> ORGANISM: Homo sapiens

<400> SEQUENCE: 34

Phe Phe Val Ala Leu Phe Pro Glu Val Phe Gly Lys
1               5                   10

<210> SEQ ID NO 35
<211> LENGTH: 5
<212> TYPE: PRT
<213> ORGANISM: Homo sapiens

<400> SEQUENCE: 35

Gln Phe Tyr Gln Leu
1               5

<210> SEQ ID NO 36
<211> LENGTH: 11
<212> TYPE: PRT
<213> ORGANISM: Homo sapiens

<400> SEQUENCE: 36

-continued

```
Ala Val Pro Tyr Pro Gln Arg Asp Met Pro Ile
 1           5                   10
```

US 7,189,823 B2

ANTIBODY AGAINST ILLFDYFNR

This application is a continuation of U.S. patent application Ser. No. 10/350,367, filed Jan. 24, 2003 now abandonded, which claims the benefit of U.S. Provisional Patent Appl. No. 60/351,819, filed Jan. 25, 2002, and U.S. Provisional Patent Appl. No. 60/412,612, filed Sep. 19, 2002.

STATEMENT REGARDING GOVERNMENT SPONSORED RESEARCH

This invention was made with government support from the United States National Institutes of Health. The government may have certain rights in this invention.

BACKGROUND OF THE INVENTION

The present invention relates generally to proteins associated with cell proliferative disorders of the colon including primary colon cancer and colon cancer metastases to liver. The invention also relates to proteins associated with normal colon tissue.

Improvements in surgical procedures, adjuvant therapies, and screening programs have facilitated an overall decline in the mortality of colon cancer in the last 20 years (1). Colorectal cancer nevertheless remains a significant disease accounting for 11% of all cancers in the United States with an estimated 130,200 new cases and 48,100 deaths expected in the year 2001 (2). When diagnosed at an early localized stage, five-year survival of colon cancer is 90%. Only 37% of incident cases are diagnosed at this stage, the remainder often presenting to a physician when the tumor has become metastatic.

More effective screening and prevention measures for colorectal cancer are needed to address this public health problem. Early detection procedures for colorectal cancer have included tests for fecal blood or use of endoscopy. The fecal blood test requires significant tumor size (sensitivity of 90% for small polyps and 75% for diminutive polyps) and has a sensitivity of about 26%, which means 74% of patients with malignant lesions will remain undetected (3). The fecal occult blood test fails to detect many early stage colon cancers because little if any blood is released into the stool at that stage. Also the fecal occult test is not very specific as a general screen, subjecting many to needless discomfort and risk in subsequent full bowel examination.

Visualization of precancerous and cancerous lesions by endoscopy is effective in early detection but is an invasive method with attendant significant risk of complications (4,5). For example, the cecum is reached in 80%–95% of procedures (22) and incomplete colonoscopies require either a repeat colonoscopy or supplemental barium enema.

The complications and cost of the colonoscopy are considerable and the appropriate frequently at which this procedure should be used for cancer screening tool is unknown. Furthermore, the procedural competence varies considerably among endoscopists. Thus, colonoscopy is presently not useful for screening the general population for colon cancer.

Much effort over the years has been directed to the identification of improved diagnostic markers for colon cancer that enable reliable early cancer detection or provide early prognostic information. Carcinoembryonic antigen (CEA), which is a tumor-associated glycoprotein, was found to be expressed at increased levels in 95% of colorectal, gastric and pancreatic cancers, and in the majority of breast, lung and head and neck carcinomas (6). Diagnostic blood tests for CEA are in use for following the course of therapy in the management of colorectal cancer. In postoperative follow-up, CEA appears to be a useful marker of recurrence (sensitivity, 77%; specificity 98%), mainly for liver metastasis, but it has also been shown that only half of colorectal cancers shed CEA levels sufficient for their detection in monitoring therapy (7,8).

The utility of CEA in detecting recurrences is controversial and has yet to be widely applied (9,10). Elevated CEA levels have been reported in patients with nonmalignant disease and many patients with colon cancer have normal CEA levels in the serum, especially during the early stage of the disease (7,11). In light of the currently available data, serum CEA determination possesses neither the sensitivity or specificity needed as an early screening test for colorectal cancer in the asymptomatic population (12).

Changes in nuclear shape, size and DNA organization including major morphological transformation are unique characteristics of cancer cells has been used to diagnose cancer. Nuclear structure is determined by the scaffolding of the nucleus, the nuclear matrix. The nuclear matrix consists of the peripheral lamins, protein complexes, an internal ribonucleic protein network, and residual nucleoli (23). The nuclear framework consists of approximately 10% of the nuclear proteins, and is virtually devoid of lipids, DNA, and histones (24). Most of the nuclear matrix proteins identified to date are common to all cell types, but several identified NMPs are tissue and cell line specific and NMPs have been shown to undergo change with differentiation (25, 26).

Cell type-specific "fingerprinting" of aberrant nuclear matrix proteins and their appearance in cancer development has led to the analysis of nuclear matrix protein composition of a variety of tumors in an effort to determine whether these proteins can be developed as diagnostic and/or prognostic markers for cancer. By means of high resolution, two-dimensional electrophoresis, specific nuclear matrix protein alterations have been demonstrated to exist in primary cancers of the prostate, bladder, renal and colon (27–30). The detection of nuclear matrix proteins in the serum of patients with various types of cancer has been accomplished (31).

SUMMARY OF THE INVENTION

In accordance with one aspect of the invention, there is provided a purified protein present in cancerous colon cells but absent or reduced in amount in normal colonic epithelial cells. The specified proteins include, CC2, CC3, CC4, CC5, CC6a, CC6b, L1, L2 and L5. The apparent molecular weight, isoelectric point and partial amino acid sequence for these proteins are provided in the context of the examples herein. In a preferred embodiment the proteins are detected in nuclear matrix preparations ("NMPs").

In accordance with another aspect of the invention, proteins are provided that are present in normal epithelial colonic cells but that are absent or present in reduced amount in cancerous colon cells. The specified proteins include N1–N6, the apparent molecular weight, and isoelectric point of which are provided (see Examples, infra). In a preferred embodiment, the N proteins are detected in nuclear matrix preparations.

In accordance with yet another aspect of the invention, there is provided purified proteins in cancerous colon cells and liver metastasis derived therefrom which are useful as colon cancer diagnostic markers. The specified proteins include L1, L2, L3, L4 and L5, the apparent molecular weight and isoelectric point of which are provided below. In a preferred embodiment, proteins L1–L5 are detected in NMPs.

In accordance with a further aspect of the invention, there is provided binding partners specific for the invention proteins. The binding partners may be used, for example, for diagnostic or therapeutic purposes. Methods of producing binding partners are provided. The binding partner preferably is a monoclonal or polyclonal antibody.

In accordance with yet a further aspect of the invention, a method is provided for diagnosing in a patient a cell proliferative disorder of the colon, preferably colon cancer, by analyzing tissue, stool, or body fluid from the patient for the presence of at least one protein that is present in cancerous colonic cells but absent or reduced in amount in normal colonic epithelial cells, or that is present in normal colonic epithelial cells but absent or reduced in amount in cancerous colonic cells. Such diagnostic proteins include, CC2, CC3, CC4, CC5, CC6a, CC6b, L1, L2 and L5 and N1-N6. The proteins may be detected by any of a variety of means including biochemical means such as 2-D gel electrophoresis, detection with a specific binding partner or by determining the level of encoding mRNA. In one embodiment, the proliferative disorder is colorectal adenocarcinoma while in another embodiment, the proliferative disorder is colonic adenoma.

In accordance with still yet a further aspect of the invention, there is provided a method of diagnosing colon cancer in a patient comprising analyzing tissue, stool or body fluid from the patient for the presence of calreticulin. Calreticulin may be detected by any of a variety of means including biochemical means such as 2-D gel electrophoresis, detection with a specific binding partner or by determining the level of encoding mRNA. In a preferred embodiment, calreticulin is detected in NMP preparations.

In accordance with another aspect of the invention, there is provided a method of evaluating colonic adenomas for potential to become malignant. The method comprises analyzing the adenoma for the presence of at least one protein that is present in cancerous colonic cells but absent or reduced in amount in normal colonic epithelial cells, or present in normal colonic epithelial cells but absent or reduced in amount in cancerous colonic cells. The proteins are CC2, CC3, CC4, CC5, CC6a, CC6b, L1, L2 and L5 and N1–N6. In a preferred embodiment, the proteins are CC3, CC4, and CC5. The proteins may be detected by any of a variety of means including biochemical means such as 2-D gel electrophoresis, detection with a specific binding partner or by determining the level of encoding mRNA.

In accordance with a further aspect of the invention, there is provided a method of diagnosing colon cancer to liver metastasis in a patient. The method comprises analyzing a sample of liver for the presence of at least one protein, wherein the protein is any of L1–L5. The proteins may be detected by any of a variety of means including biochemical means such as 2-D gel electrophoresis, detection with a specific binding partner or by determining the level of encoding mRNA.

DETAILED DESCRIPTION OF THE INVENTION

As noted, a key aspect of the present invention is the inventor's provides a purified protein that is present in cancerous colon cells but absent or reduced in amount in normal colonic epithelial cells. These proteins along with their apparent molecular weight (defined by SDS-PAGE) and isoelectric point are as follows:

a) CC2 having a molecular weight of about 56 kD and a pI of about 6.22;
b) CC3 having a molecular weight of about 43 kD and a pI of about 6.3;
c) CC4 having a molecular weight of about 43 kD and a pI of about 6.2;
d) CC5 having a molecular weight of about 42 kD and a pI of about 6.2;
e) CC6a having a molecular weight of about 20 kD and a pI of about 6.9;
f) CC6b having a molecular weight of about 20 kD and a pI of about 6.8.
g) L1 having a molecular weight of about 50 kD and a pI of about 6.01;
h) L2 having a molecular weight of about 20 kD and a pI of about 5.73; and
i) L5 having a molecular weight of about 19 kD and a pI of about 5.88.

These proteins also may be defined by amino acid sequence shown in Tables 5, 6 and 9, and by presence in a NMP preparation. For example, in the case of CC2, it is defined as comprising one or more proteins having a molecular weight of about 56 kD and an isoelectric point of about 6.22, wherein the protein comprises amino acid sequence from any one or more of SEQ ID NOs: 14–17 and 23. Thus, CC2 can be defined by its molecular weight and pI, its presence in an NMP preparation, and by SEQ ID NO: 14, SEQ ID NO: 15, SEQ ID NO: 16, SEQ ID NO: 17, or SEQ ID NO: 23, or any combination of these sequences.

Also provided is a purified protein that is present in normal epithelial colonic cells but absent or reduced in amount in cancerous colon cells. These proteins along with their apparent molecular weight (defined by SDS-PAGE) and isoelectric point are as follows:

a) N1 having a molecular weight of about 40 kD and a pI of about 5.5;
b) N2 having a molecular weight of about 30 kD and a pI of about 5.94;
c) N3 having a molecular weight of about 30 kD and a pI of about 5.88;
d) N4 having a molecular weight of about 30 kD and a pI of about 5.80;
e) N5 having a molecular weight of about 30 kD and a pI of about 5.73; and
f) N6 having a molecular weight of about 18 kD and a pI of about 6.6.

Proteins N1–N5 can be defined by their molecular weight and pI, and presence in an NMP preparation.

Further provided are various purified proteins useful as diagnostic markers for colon cancer metastases to the liver. These proteins along with their apparent molecular weight (defined by SDS-PAGE) and isoelectric point are as follows:

a) L1 having a molecular weight of about 50 kD and a pI of about 6.01;
b) L2 having a molecular weight of about 20 kD and a pI of about 5.73;
c) L3 having a molecular weight of about 17 kD and a pI of about 6.09;
d) L4 having a molecular weight of about 17 kD and a pI of about 6.00; and
e) L5 having a molecular weight of about 19 kD and a pI of about 5.88.

L1–L5 are useful as diagnostic markers of colon cancer metastatic to liver because these proteins are more detectable in samples of liver that contain colon cancer than in samples of normal liver tissue. These proteins may be defined by their molecular weight and pI, their presence in an NMP prepration and by amino acid sequence as shown in Table 9.

As used herein, the term "absent or reduced in amount in normal colonic epithelial cells" means that the protein is not detectable in normal colonic epithelial cells or is detectable in such cells but at a lower level than that for colorectal carcinoma cells. In being more detectable in colorectal carcinoma versus normal colonic epithelial cells, the protein can be detected in 80% or more of cancer samples versus 50% or less for comparable non-cancer samples. Similarly, in connection with proteins that are markers of colon cancer to liver metastases, the term absent or reduced in amount means that the proteins are more detectable in samples of liver that contain colon cancer than in samples of normal liver tissue. In being "more detectable, proteins L1–L5 are detectable in 80% of colon to liver metastases versus 50% or less for donor samples of normal liver tissue.

The increased detectability of L1–L5 in metastatic colon to liver tissue versus normal liver tissue is believed to result from an increased level of expression of these proteins in colon cancer cells versus normal liver cells including hepatocytes. "Normal liver tissue" includes "normal donor liver tissue," which refers to liver tissue from a donor that does not have metastatic liver cancer and "adjacent normal liver tissue," which refers to normal liver tissue from a liver with colon cancer metastasis. The term "adjacent" is used to identify the type of liver from which this "normal" liver tissue is obtained (i.e. metastatic liver) rather than to indicate any degree of proximity between such normal tissue and the metastatic cancer.

The percentage of 2D gels in which L1–L5 were detected in samples of liver containing colon cancer metastases and in samples containing normal liver tissue is shown in Table 7, (Example 5). Although L3 and L4 proteins were detected in normal adjacent liver and in normal donor liver, the amount of protein detected was qualitatively speaking lower in amount that in the cancer metastatic tissue.

Protein identification by silver stained—high-resolution, two-dimensional gel electrophoresis analysis of nuclear matrix preparations is a preferred method for determining whether the invention proteins are more detectable in a particular tissue than in another tissue. Other approaches are possible and include detection of the proteins in the tissue or in tissue extracts using a binding partner specific for the protein or by detecting RNA encoding the protein.

In this description, the phrase "nuclear matrix" refers to a 3-dimensional filamentous protein network that is present in the interphase nucleus. The NMPs of the protein network provide a framework to maintain the overall size and shape of the nucleus and acts a structural attachment site for the DNA loops during interphase.

An "NMP preparation" is a preparation from a biological source (e.g., a cell, tissue or body fluid) that is enriched in nuclear matrix proteins ("NMPs"). "Enriched" means that at least some NMP are present at a higher frequency in the NMP that they are in the natural state (e.g., in cell, tissue, or biological fluid). NMP preparations may be prepared by well known methods in the art such as detergent and urea extraction (see Getzenberg et al. reference 29). An NMP preparation that is enriched in NMPs may contain proteins that are not part of the nuclear matrix The present invention provides binding partners specific for the invention proteins. The binding partners are useful to detect the presence of the protein in a sample. The protein and its binding partner represent a binding pair of molecules, which interact with each other through any of a variety of molecular forces including, for example, ionic, covalent, hydrophobic, van der waals, and hydrogen bonding, so that the pair have the property of binding specifically to each other. Specific binding means that the binding pair exhibit binding with each other under conditions where they do not bind to another molecule. Examples of types of specific binding pairs are antigen-antibody, biotin-avidin, hormone-receptor, receptor-ligand, enzyme-substrate, IgG-protein A, and the like. A preferred binding partner for the proteins of the invention is an antibody, but other desirable binding partners may comprise a nucleic acid (e.g. natural or synthetic DNA, RNA, gDNA, cDNA, mRNA, tRNA, etc.), a lectin, an oligosaccharide, a glycoprotein, a drug candidates (from, for example, a random peptide library, a natural products library, a lectin library, a combinatorial library, an oligosaccharide library or a phage display library), a metabolite, a vitamin, a lipid, a steroid, a metal, and the like.

In the present context, an "antibody" is a protein that is made up of one or more polypeptides, substantially encoded by immunoglobulin genes or fragments of such genes. The recognized immunoglobulin genes include the kappa, lambda, alpha, gamma, delta, epsilon and mu constant region genes, as well as a myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) is a tetramer composed of two identical pairs "light" chains (each about 25 kD) and two identical pairs of "heavy" chains (each about 50–70 kD). The N-terminus of each chain defines a variable region of about 100 to 110 or more amino acids primarily responsible for antigen recognition. The terms "variable light chain" (VL) and "variable heavy chain" (VH) refer to the variable portions of the light and heavy chains, respectively. The antigen-recognition site or ligand/substrate-binding site of an immunoglobulin molecule is formed by three highly divergent stretches within the V regions of the heavy and light chains known as the "hypervariable regions," which are interposed between more conserved flanking stretches known as "framework regions." In an antibody molecule, the three hypervariable regions of a light chain and the three hypervariable regions of a heavy chain are disposed relative to each other in three dimensional space to form an antigen binding surface. This surface mediates recognition and binding of the target antigen or ligand/substrate. The three hypervariable regions of each of the heavy and light chains are referred to as "complementarily determining regions" or "CDRs" and are discussed, for example, by Kabat et al. (15). The portion of the antigen that interacts with the CDRs of the antibody is referred to as an epitope.

Antibodies exist as intact immunoglobulins or as a number of well-characterized fragments, such as those produced by digestion with various peptidases and those that can be made by recombinant DNA technology. Antibody fragments include Fab' monomer, Fab'2 dimer, Fv fragment, single chain Fv ("scFv") fragment, and the like. See e.g., Huston et al., (16). Antibody fragments also include antibody forms having a truncated or deleted segment of the light and/or heavy chain constant region.

Antibodies of the present invention may be monoclonal or polyclonal. In general polyclonal antibodies are present in the sera of animals immunized by one or more injections of the invention proteins or fragments thereof. In general, monoclonal antibodies are prepared by obtaining a source of B cells from a suitably immunized animal, immortalizing the B cells, cloning populations of B cells from individual immortalized cells, and selecting clones making an antibody of interest. Methods for making polyclonal antibodies and monoclonal antibodies are well known in the art. For example, see Harlow and Lane (17).

Accordingly, a method is provided for producing polyclonal antibodies that differentiate primary colon cancer from normal colon and/or colon cancer liver metastases from normal liver tissue. The method comprises immunizing an animal with one or more of the invention proteins and recovering the antibodies. There is further provided a method of producing a monoclonal antibody that differentiate primary colon cancer from normal colon and/or colon cancer liver metastases from normal liver tissue. The method comprises immunizing an animal with one or more of the invention proteins, removing B cells from the immunized animal and immortalizing and isolating the B cells that produce an antibody specific for the protein. As an alternative to immortalization, nucleic acid encoding antibody heavy and light chains may be obtained from immune cells of the immunized animal. The nucleic acid can then be cloned into appropriate expression vectors and used to transform, transfect or otherwise transduce host cells so that the host cells produce antibody derived from the heavy and light chains present in B cells of the immunized animal. Host cells producing antibodies of interest may be selected.

An immunogen suitable for eliciting specific antibodies to the invention proteins can comprise a purified or a partially purified preparation of the protein. A purified protein of the invention is at least 20% pure, preferably at least 40% pure, more preferably at least 60% pure, even more preferably at least 80% pure and still even more preferably at least 90% and most preferably at least about between 95 and 99% pure.

The terms "protein," "polypeptide," and "peptide" are used interchangeably in this description to denote a polymer of amino acid residues. The category of "protein" includes proteins associated with other molecules, such as a glycoprotein, a proteoglycan, a lipoprotein, a nucleic acid, and combinations thereof. Unless otherwise specified, the terms "a," "an" or "the" mean one or more. The proteins of the invention also include conservatively substituted variants thereof. Minor modifications of the primary amino acid sequence may result in proteins that have substantially equivalent activity as compared to the natural polypeptide described herein. Conservative substitutions in sequence, which denote the replacement of an amino acid residue by a structurally similar residue, are preferred. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Such modifications may be deliberate, as by site-directed mutagenesis, or may be spontaneous, and can include deletion of non-essential amino acids. Modification includes deletion of one or more amino acids, which may be used to develop a smaller active molecule that has broader utility. All of the polypeptides produced by these modifications are included herein as long as the biological activity of the native protein remains the same. The proteins of the invention also include fragments of the protein which are useful, for example, to generate binding partners for the protein.

An NMP preparation can be used as a source of partially purified protein for the immunogen. The invention proteins may be purified by any of a number of well-known purification procedures, including precipitation, chromatography, electrophoresis, immunological separations involving monoclonal or polyclonal antibodies, and the like. For example, a purified protein preparation can be obtained by 2-D gel electrophoresis of an NMP followed by excising the protein spot and using electrophoresis to elute the protein from the gel (see Examples). Alternatively, the proteins or their fragments may be synthesized by the well-known solid phase peptide synthesis methods described, for example, by Merrifield (13) or by Stewart and Young (14), based on protein sequences.

Purified preparations of the invention proteins or fragments thereof also may be prepared by recombinant expression using vectors and host cells well known in the art and commercially available such as are described in Goeddel et al. (18). Host cells include, for example, mammalian, bacterial, yeast, and the like. The host cell may be transformed with recombinant DNA by conventional techniques known in the art. For example, where the host is prokaryotic, such as $E.\ coli$, one can prepare competent cells, which are capable of DNA uptake, from cells harvested after the exponential growth phase and subsequently treated by the $CaCl_2$ method, by conventional procedures. Transformation also can be performed by forming a protoplast of the host cell or by electroporation. A eukaryotic host may be transformed with foreign DNA using well known procedures such as by calcium phosphate coprecipitation, microinjection, electroporation, encasement in liposomes, virus vectors, and the like. Recombinant DNA also may be introduced by transfection and transduction methods well known in the art.

Eukaryotic cells can also be co-transformed with DNA sequences encoding the proteins of the invention, and a second foreign DNA molecule encoding a selectable phenotype, such as the herpes simplex thymidine kinase gene. Another method is to use a eukaryotic viral vector, such as simian virus 40 (5V40) or bovine papilloma virus, to transiently infect or transform eukaryotic cells and express the protein.

The invention proteins or fragments thereof may be expressed as a fusion to a foreign polypeptide, for example, a bacterial ligand binding sequence such as GST or Staphylococcal Protein A. Fusion to GST, for example, provides an efficient means to purify the fusion product or increase its immunogenicity (see, e.g., Uhlen and Moks, (19)). Immunogenicity may also be enhanced by chemically coupling the protein or fragment to a suitable immunogenic carrier protein. Carrier proteins useful for the present invention have molecular weights of at least about 20,000 Daltons. Carrier proteins useful in the present invention include, for example, GST, hemocyanins such as from the keyhole limpet, serum albumin or cationized serum albumin, thyroglobulin, ovalbumin, various toxoid proteins such a tetanus toxoid or diphtheria toxoid, immunoglobulins or heat shock proteins. Methods to chemically couple a polypeptide to a carrier protein are well known in the art and include conjugation by a water soluble carbodiimide such as 1-ethyl-3-(3-dimethylaminopropyl)carbodiimide hydrochloride, conjugation by a homobifunctional cross-linker having, for example, NHS ester groups or sulfo-NHS ester analogs, conjugation by a heterobifunctional cross-linker having, for example, and NHS ester and a maleimide group such as sulfosuccinimidyl-4-(N-maleimidomethyl) cyclohexane-1-carboxylate, conjugation with gluteraldehyde, and the like. For example, see Hermanson, (20) and U.S. Pat. No. 4,608,251 and No. 4,161,519.

Binding partners such as polyclonal or monoclonal antibodies can be used to detect the invention proteins in immunoassays such as RIA, EIA, and the like. Such assays may be competitive or non-competitive and may based on a direct or an indirect format. The binding partner can be used in liquid phase and/or bound to a solid-phase carrier. Carriers include glass, polystyrene, polypropylene, polyethylene, dextran, nylon, natural and modified cellulose, polyacrylamide, agarose, magnetite, and the like. The nature of the carrier can be either soluble or insoluble. As is typical of immunoassays, the binding partner or the invention protein may be detectably labeled in any of various ways well known in the art. Binding partners also may be used to detect the invention proteins in electrophoretically dispersed gels (e.g., a 2-D gel) or attached to a solid phase membrane such as a Western blot.

An immunogen comprising the invention proteins or fragments thereof may also be administered with an adjuvant either by mixing with the protein or fragment or by conjugating or otherwise linking to the adjuvant. A variety of adjuvants are known including Freund's (complete and incomplete), alum, muramyl dipeptide, BCG, LPS, Ribi Adjuvant System®, TiterMax®, and the like. One skilled in the art would know which type of adjuvant is appropriate to use in a given circumstance.

The present invention also provides a method of diagnosing a proliferative disorder of the colon in a patient, the method comprising: analyzing tissue, stool or body fluid from the patient for the presence of at least one protein that is present in cancerous colonic cells but absent or reduced in amount in normal colonic epithelial cells, or present in normal colonic epithelial cells but absent or reduced in amount in cancerous colonic cells, wherein the protein is selected from the group consisting of:
a) CC2 having a molecular weight of about 56 kD and a pI of about 6.22;
b) CC3 having a molecular weight of about 43 kD and a pI of about 6.3;
c) CC4 having a molecular weight of about 43 kD and a pI of about 6.2;
d) CC5 having a molecular weight of about 42 kD and a pI of about 6.2;
e) CC6a having a molecular weight of about 20 kD and a pI of about 6.9;
f) CC6b having a molecular weight of about 20 kD and a pI of about 6.8.
g) L1 having a molecular weight of about 50 kD and a pI of about 6.01;
h) L2 having a molecular weight of about 20 kD and a pI of about 5.73;
i) L5 having a molecular weight of about 19 kD and a pI of about 5.88;
j) N1 having a molecular weight of about 40 kD and a pI of about 5.5;
k) N2 having a molecular weight of about 30 kD and a pI of about 5.94;
l) N3 having a molecular weight of about 30 kD and a pI of about 5.88;
m) N4 having a molecular weight of about 30 kD and a pI of about 5.80;
n) N5 having a molecular weight of about 30 kD and a pI of about 5.73; and
o) N6 having a molecular weight of about 18 kD and a pI of about 6.6.

As already described, the protein may be detected by any of a variety of means including biochemical means such as 2-D gel electrophoresis, detection with a specific binding partner such as a monoclonal or polyclonal antibody, and the like. The protein also may be detected by determining the level of mRNA encoding the protein through hybridization with an appropriate oligonucleotide probe. A "patient" in this regard is a mammal, preferably a human.

In this description, the phrase "proliferative disorder of the colon" denotes malignant as well as non-malignant (or benign) disorders of the colon, including but not limited to the colonic epithelium. Such disorders include polyps such as with atypia or dysplasia, sessile villous adenomas, pedunculated tubular adenomas, and the like. The cells comprising these proliferative disorders often appear morphologically and genotypically to differ from the surrounding normal tissue. The proliferative disorder may be associated, for example, with expression of the CC or L proteins of the invention, in the latter case, particularly L1, L2 and L5. Expression of a protein identified herein at an inappropriate time during the cell cycle or in an incorrect cell type may result in a cell-proliferative disorder. The protein-encoding polynucleotide in the form of an antisense polynucleotide (or ribozyme) is useful in treating hyperplasia and malignancies of the colon. In a preferred embodiment, the proliferative disorder is colon cancer. Table 2 (Example 2) shows the percentage of 2-D gels in which L1, L2 and L5 were detected in nuclear matrix preparations of normal adjacent colonic tissue and normal donor colonic tissue.

Also provided herein is a method of evaluating colonic adenomas for potential to become malignant, the method comprising: analyzing the adenoma for the presence of at least one protein that is present in cancerous colonic cells but absent or reduced in amount in normal colonic epithelial cells, or present in normal colonic epithelial cells but absent or reduced in amount in cancerous colonic cells, wherein the protein is selected from the group consisting of:
a) CC2 having a molecular weight of about 56 kD and a pI of about 6.22;
b) CC3 having a molecular weight of about 43 kD and a pI of about 6.3;
c) CC4 having a molecular weight of about 43 kD and a pI of about 6.2;
d) CC5 having a molecular weight of about 42 kD and a pI of about 6.2;
e) CC6a having a molecular weight of about 20 kD and a pI of about 6.9;
f) CC6b having a molecular weight of about 20 kD and a pI of about 6.8.
g) L1 having a molecular weight of about 50 kD and a pI of about 6.01;
h) L2 having a molecular weight of about 20 kD and a pI of about 5.73;
i) L5 having a molecular weight of about 19 kD and a pI of about 5.88;
j) N1 having a molecular weight of about 40 kD and a pI of about 5.5;
k) N2 having a molecular weight of about 30 kD and a pI of about 5.94;
l) N3 having a molecular weight of about 30 kD and a pI of about 5.88;
m) N4 having a molecular weight of about 30 kD and a pI of about 5.80;
n) N5 having a molecular weight of about 30 kD and a pI of about 5.73; and
o) N6 having a molecular weight of about 18 kD and a pI of about 6.6; wherein detection of said proteins indicates an increased potential to become malignant. In a preferred embodiment, the proteins are CC3, CC4 and CC5.

The invention also contemplates the diagnosing of colon cancer to liver metastasis in a patient, by analyzing tissue or body fluid from the patient for the presence of at least one protein selected from the group consisting of:
a) L1 having a molecular weight of about 50 kD and a pI of about 6.01;
b) L2 having a molecular weight of about 20 kD and a pI of about 5.73;
c) L3 having a molecular weight of about 17 kD and a pI of about 6.09;
d) L4 having a molecular weight of about 17 kD and a pI of about 6.00; and
e) L5 having a molecular weight of about 19 kD and a pI of about 5.88.

Detection of proteins according to the present invention can allow differentiation among colonic cell proliferative disorders that have a potential to become malignant or to metastasize, respectively. The protein compositions described herein also are useful as markers for early diagnosis of a colonic cell proliferative disorder such as colorectal cancer and the early detection of recurrence, and its metastastic diseases derived therefrom, knowledge that is central to the effective treatment of this disease. In addition to their use individually, detection of any two or more invention proteins can be combined to diagnose proliferative disorders of the colon including colon cancer and its liver metastases. Detection of the invention proteins also may be combined with detecting other colon cancer markers, such as CEA or previously reported colon cancer NMPs (32), to diagnose the colon cancer and its liver metastases.

The particular proteins or fragments described herein may be detected indirectly, for example, by detecting the level of encoding mRNA. Thus, the present invention provides a purified polynucleotide sequence encoding the above-identified protein or fragments of the preceding embodiments. Also provided is a nucleic acid probe that hybridizes to the polynucleotide sequence encoding the above-mentioned protein or fragments thereof (or by hybridization to the complementary sequence). The term "nucleic acid" as used herein refers to a deoxyribonucleotide or ribonucleotide polymer in either single—or double-stranded form, and also encompasses known analogs of natural nucleotides that can function in a similar manner as naturally occurring nucleotides. The probe is preferably single stranded and preferably comprises at least about 14 nucleotides in length, more preferably at least about 18 nucleotides in length, and most preferably about 25 nucleotides in length. The nucleic acid probe can be detectably labeled such as with a radioisotope, a bioluminescent compound, a chemiluminescent compound, a fluorescent compound, a metal chelate, an enzyme, and the like.

Also provided is a kit for detecting a colonic cell proliferative disorder. The kit may include a binding partner or nucleic acid probe that is specific for any one or more of the invention proteins. The binding partner or probe can be labeled for ease of detection. The kit may have reagents in different vials and may include positive and negative controls, buffers such as for conducting the reactions, and a directional insert. The kit also may have an oligonucleotide primer that permits amplification of a target polynucleotide sequence encoding one of the invention proteins, for example, by polymerase chain reaction (PCR) amplification.

The present invention also provides methods to treat colon cancer and its liver metastases, by reducing the level of expression or activity of a protein which is present primary colon cancer cells and liver metastases derived therefrom. Such proteins include any of the CC or L proteins disclosed herein. The level of expression of the protein can be reduced, for example, by treating the individual with an antisense nucleic acid or a ribozyme.

An antisense nucleic acid is a short DNA or RNA oligonucleotide designed to be complementary to a specific gene sequence. The purpose in using antisense to alter specific gene expression resulting from the binding of the antisense oligonucleotide to the gene sequence. Antisense molecules that bind to a specific region of the DNA helix may result in triplex formation since a third strand is formed at the site of binding to the two stands comprising the helix. Antisense oligonucleotides that target RNA may be either non-catalytic or catalytic (i.e., ribozymes). Binding of non-catalytic antisense molecules to the target RNA can block further RNA processing or transport through any of several possible mechanisms, including, for example: 1) transient inhibition by the prevention of ribosome binding to the RNA by masking its binding site on the mRNA; 2) permanent inhibition of the process by which RNase H degrades RNA in RNA/DNAs hybrids, an enzyme present in most cells; and 3) permanent inhibition by cross-linking the oligonucleotide to the target RNA.

The antisense compounds preferably comprise between about 8 to about 30 nucleobases (i.e., from about 8 to about 30 linked nucleosides), and more preferably from about 12 to about 25 nucleobases. The antisense oligonucleotide can be linear or circular in configuration. Antisense compounds useful herein may include oligonucleotides containing modified backbones or non-natural internucleoside linkages. Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3-5' to 5'-3' or 2'–5' to 5'-2'. Extensive citation to methods of preparing antisense oligonucleotides can be found, for example, in U.S. Pat. No. 6,210,892 to Bennett.

Where the cell proliferative disorder is characterized as having under-expression of an invention protein (e.g., N1 or N6) a polynucleotide sequence encoding the missing underexpressed protein (such as for a growth or tumor suppressor protein) can be administered to increase the level of expression. This can be achieved by introducing into the cells of a host subject an expression vector comprising a polynucleotide sequence encoding any one or more of the invention proteins. Preferably, the expression vector is introduced into the cells of the host subject ex vivo, yielding transformed cells, and the transformed cells are then reintroduced into the subject. This can be achieved, for example, with an RNA virus vector such as a retroviral vector. Cells transformed to express the proteins are also useful, for example, as a tumor vaccine. Methods of preparing vectors for delivering sense or antisense nucleic acid into cells (in vivo or in vitro) and methods of formulating these delivery vehicles for administration are well known in the art. See, e.g., U.S. Pat. No. 5,824,490 to Coffey et al.

The level of expression of the invention protein also can be reduced by treating the individual with a compound that effects a regulatory region controlling expression such a promoter or an enhancer or that modulates the activity of the proteins. Such compounds may be identified by a) incubating the proliferative cells (e.g., colorectal cancer cells) expressing the invention protein with a test composition under conditions that allow the cells and test composition to interact, and (b) measuring whether the test composition blocks or enhances the function of the protein. Caco-2 cells are an example of a colorectal cancer cell line that is useful in this regard.

The invention will be described in greater detail by reference to the following non-limiting examples.

EXAMPLES

Example 1

Methods for Isolation and Purification of NMPs

A. Tissue Processing:

Colon adenocarcinoma liver, metastases samples (N=12) and matched adjacent normal liver tissues (N=12) were collected through the Early Detection Research Network (EDRN) of the University of Pittsburgh Medical Center under institutional IRB approval. The patients ranged in age from 44–75 with a mean age of 62.4 years. Sixty percent of the sample population was female. The carcinomas, staged according the standard TNM system, were categorized as shown in Table 1.

Colon adenocarcinoma samples (N=10) and matched adjacent normal liver tissues (N=10) also were collected through the Early Detection Research Network (EDRN) of the University of Pittsburgh Medical Center under institutional IRB approval. The patients ranged in age from 36–82 with a mean age of 71 years. Sixty percent of the sample population was female. Staging for these carcinomas categorized as shown in Table 1.

TABLE 1

Stage and UI Grade of Colon Carcinoma Tumors Used for NMP Preparation

| Clinical Parameter | Result (number of samples) |
|---|---|
| Tumor location | Right hemicolon (n = 5) |
| | Left heimcolon (n = 5) |
| Tumor Stage (UICC) | I: $T_{1-2}N_0M_0$ (n = 0) |
| | II: $T_{3-4} N_0M_0$ (n = 5) |
| | III: $T_{1-4}N_{1-2}M_0$ (n = 4) |
| | IV: $T_{1-4}N_{1-2}M_1$ (n = 1) |
| Tumor Grade | G1 (n = 0) |
| | G2 (n = 9) |
| | G3 (n = 1) |

Normal liver tissue was obtained from trauma victims including one sample from a gunshot victim and two from an automobile accident victim (N=3). The patients ranged in age from 36–48 with a mean age of 40.3 years. Two of these normal individuals were male and one female. None of the patients had liver cirrhosis. Thirty percent of the patients had mild steatosis. Diagnosis was obtained from pathology reports, which accompanied each specimen and was confirmed histologically. Tissues were stored at −80° C. prior to processing. Sporadic colon adenocarcinoma samples and matched adjacent normal tissues and normal donor colon tissues were collected as previously described (30).

Normal colon tissue was obtained from trauma victims; Two of these individuals had gunshot wounds, one suffered from automobile trauma and one was an organ donor (N=4). The patients ranged in age from 20–59 with a mean age of 47.2 years. The normal colon donors were all male. Diagnosis was obtained from pathology reports, which accompanied each specimen and was confirmed histologically.

The colon cancer cell lines, SW480 and Caco-2, were obtained from the American Type Culture Collection (Manassas, Va.). Both cell lines were established from primary human colon cancer cells. The SW480 cell line was grown in Leibovitz medium with 10% fetal bovine serum at 37° C. without $CO_2$. The Caco-2 cell line was grown in Dulbecco's minimal essential medium (DMEM) supplemented with 10% fetal bovine serum, 1% L-glutamine (200 mM), 1% penicillin/streptomycin, 1% sodium pyruvate (100 mM), 1% MEN non-essential amino acids, 1.5% HEPES Buffer (1M) at 37° C. in a 5% $CO_2$ atmosphere.

The colon cancer cell line CX-1 was a kind gift from Lee Y J Ph.D. University of Pittsburgh. The cell line has been established from primary human colon cancer cells. The cell line was grown in RPMI-1640 media with 10% fetal bovine serum and 1% penicillin/streptomycin at 37° C. in a 5% $CO_2$ atmosphere.

Normal human hepatocytes ($50\times10^6$), obtained from a 63 year-old female organ donor, were a gift from Dr. Stephen Strom (University of Pittsburgh, Pa). Human primary liver cancer cell lines, huh 7, HepG 2, were a kind of gift of Dr. George Michalopoulos, University of Pittsburg, Pa. Both cell lines were grown in DMEM with 10% fetal bovine serum and 1% penicillin/streptomycin at 37° C. in a 5% $CO_2$ atmosphere.

B. Nuclear Matrix Preparation:

Nuclear matrix proteins were extracted from various cells and tissues according to the method of Getzenberg et al (29). In brief, tissues were finely minced into small pieces and homogenized with a Teflon® pestle on ice with 0.5% Triton X-100 in a solution containing 2 mM vanadyl ribonucleoside (Rnase inhibitor) to release the lipids and soluble proteins. The homogenate was filtered through a 350 μm nylon mesh. Treatment with DNAse and RNAse was performed to remove the soluble chromatin, resulting in a remaining fraction comprising intermediate filaments and NMPs. This fraction then was disassembled with 8 M urea, and the insoluble components consisting of carbohydrates and extracellular matrix were removed by centrifugation. After dialysis to remove the urea, intermediate filaments were allowed to reassemble and were subsequently removed by centrifligation.

The NMPs then were precipitated with ethanol and resuspended in 2D sample buffer consisting 9 M urea, 65 nM 3-((3-cholamidopropyl)-dimethyl-ammonio)-1-propane-sulfonate, 2.2% amhpolytes and 140 mM DTT, and quantitated by Coomassie Plus protein assay (Pierce Chemical Co., Rockford, Ill.) with bovine serum albumin as a standard. The pellet following ethanol precipitation containing NMPs represented <1% of the total starting cellular protein.

C. High Resolution, Two-dimensional Electrophoresis:

This procedure was performed using the Investigator 2-D gel system (Genomic Solution, Ann Arbor, Mich.) as described previously (29, 33–34). One hundred μg of protein were loaded per gel onto a capillary size IEF column. One dimensional isoelectric focusing was carried out for 18,000 volt-hours using 1 mm×18 inch tube gels after 1.5 hours of prefocusing. The tube gels were extruded and placed on top of 1 mm SDS Duracryl (Genomic Solution, Ann Arbor, Mich.) high tensile strength PAGE slab gels. The gels were electrophoresed at 12° C. constant temperature for 4.5 to 5 hours. Gels were fixed with 50% methanol and 10% acetic acid. After thorough rinsing and rehydration, gels were treated with 5% glutaraldehyde and 5 mM DTT after buffering with 50 mM Phosphate (pH 7.2). The gels were stained with silver stain using the method of Wray et al (Accurate Chemical Co., Westbury, N.Y.) (21). Molecular weights of colon NMPs were identified using standards provided by Genomic Solutions. Isoelectric points (PI's) were determined using carbamylated standards; BDH-distributed by Gallard-Schlessinger (Carle Place, N.Y.) and Sigma Chemical Co. (St. Louis, Mo.).

Multiple gels were run for each sample and multiple samples were run at different times. The gels were analyzed using the BioImage 2D Electrophoresis Analysis System (BioImage, Ann Arbor, Mich.), that matches protein spots between gels and sorts the gels and protein spots into a database. Only protein spots clearly and reproducibly identical in all gels of a sample type were taken into account as those representing the described NMP's.

Example 2

Identification of NMPs Characteristic of Colon Carcinoma or Normal Colonic Epithelium A. Analysis of NMPs from Colorectal Cancer and Normal Colonic Epithelium Evaluation of NMPs separated by high-resolution two-dimensional gel electrophoresis identified seven NMPs of clinical value that were expressed primarily in colorectal adenocarcinomas were identified and designated as shown in Table 2. CC2 to CC6a,b were strongly expressed in all colon tumors, but were undetectable in adjacent normal tissue. In contrast, CC1 was expressed in carcinoma extracts and adjacent normal or donor tissue but the signal was stronger for colon cancers than either source of normal tissue.

Six NMPs of clinical value that were expressed primarily in normal colonic epithelium were designated as shown in Table 2. N2–N6 were expressed in a minority of the colon cancers (about 20%), but were expressed in all adjacent normal and donor extracts. In contrast, N1 was expressed in most cancer extracts (about 70%) and in all normal extracts, but was more strongly but the signal was stronger for the normal extracts. The characteristics of the identified colon carcinoma NMPs are summarized in Table 2.

TABLE 2

Characteristics of Colorectal Adenocarcinoma and Normal Colonic Epithelial NMPs

| Marker No. | Molecular Weight (kD) | PI | Tissue Expression |
|---|---|---|---|
| CC1 | 59 | 4.40 | Cancer and normal epithelium but stronger for cancer (10/10 cancer; 10/10 normal adjacent; and 4/4 normal donor) |
| CC2 | 56 | 6.22 | Cancer only (8/10 cancer; 0/10 adjacent normal; and 0/4 donor normal) |
| CC3 | 43 | 6.27 | Cancer only (10/10 cancer; 0/10 adjacent normal; and 0/4 donor normal) |
| CC4 | 43 | 6.22 | Cancer only (10/10 cancer; 0/10 adjacent normal; and 0/4 donor normal) |
| CC5 | 42 | 6.25 | Cancer only (10/10 cancer; 0/10 adjacent normal; and 0/4 donor normal) |
| CC6a | 20 | 6.86 | Cancer and donor epithelium but not adjacent normal epithelium (8/10 cancer; 0/10 adjacent normal; and 4/4 donor normal) |
| CC6b | 20 | 6.81 | Cancer and donor epithelium but not adjacent normal epithelium. (8/10 cancer; 0/10 adjacent normal; and 4/4 donor normal) |
| N1 | 40 | 5.50 | Normal epithelium (adjacent and donor) and cancer (about 70% of samples) but stronger for normal (7/10 cancer; 10/10 adjacent normal; and 4/4 donor normal) |
| N2 | 30 | 5.94 | Normal epithelium mainly** (2/10 cancer; 10/10 adjacent normal; and 4/4 donor normal) |
| N3 | 30 | 5.88 | Normal epithelium mainly (2/10 cancer; 10/10 adjacent normal; and 4/4 donor normal) |
| N4 | 30 | 5.80 | Normal epithelium mainly (2/10 cancer; 10/10 adjacent normal; and 4/4 donor normal) |
| N5 | 30 | 5.73 | Normal epithelium mainly (2/10 cancer; 10/10 adjacent normal; and 4/4 donor normal) |
| N6 | 18 | 6.58 | Normal epithelium mainly (1/10 cancer; 10/10 adjacent normal; and 4/4 donor normal) |

*NC means that the reference describes nothing close in size or pI.
**Refers to an expression frequency of about 10–20% for cancer samples.

B. Analysis of CC NMPs from Colorectal Tumor Cell Lines

NMP preparations were isolated from two human colon cancer cell lines, Caco-2 and SW480, essentially as described for NMP preparation from human tissue. These NMPs were analyzed by 2 dimensional gel electrophoresis as described above for human tissue NMPs. Both cell lines expressed none of the proteins, which are expressed in the adjacent or donor gels (N1–N6). The cell line SW480 expressed the colon cancer associated proteins, CC1 and CC6a/b; the Caco-2 cell line expressed CC1, CC3, CC4, CC6a,b. CC2 was not detectable in NMP preparations of Caco2, for SW480 but was detectable in the cancer cell line CX-1. CC3, CC4 but not CC5 was detected in CX-1 NMP.

These studies demonstrate that nuclear matrix proteins isolated from human colon cancer are distinct from normal adjacent and donor tissue, indicating both loss and gain from specific proteins. The presence or absence of unique NMPs in cancer cells is useful for diagnosing disease and provide novel information about the function of NMPs in carcinogenes is.

C. Analysis of CC NMPs in Adenomatous Polyps of the Colon

Colon polyps (n=20) were collected through the Early Detection Research Network (EDRN) of the University of Pittsburgh Medical Center under institutional IRB approval. One juvenile polyp, six tubular adenoma (TA), seven tubulovillous adenoma (TVA) and six tubulovillous adenoma with high grade dysplasia (TVA with HGD) were examined. The patients ranged in age from 18 to 77 with a mean age of 58 years. 55 percent of the sample population was female. Diagnosis was obtained from pathology reports, which accompanied each specimen and was confirmed histologically. The histological partition of the colon polyps is shown in Table 3. The tissues were stored at −80° C. prior to processing.

TABLE 3

Characteristics of patients with colon polyps

| | | | |
|---|---|---|---|
| juvenile polyp | N = 1 | Age = 18 | Male 1 |
| Tubular adenoma | N = 6 | Average age = 58 | male 4; female 2 |
| Tubulovillous adenoma | N = 7 | Average age = 56 | male 1; female 7 |
| Tubulovillous adenoma with high grade dysplasia | N = 6 | Average age = 62 | male 3; female 3 |

The results for detecting the presence of CC2, CC3, CC4 and CC5 NMPs in various adenomas of the colon is shown in Table 4.

TABLE 4

Presence of CC NMPs in adenomatous colonic polyps

| Colonic abnormality | CC2 | CC3 | CC4 | CC5 |
|---|---|---|---|---|
| Tubulovillus adenoma with focal high grade dysplasia (n = 6) | 0% | 83% | 100% | 33% |
| Tubulovillus adenoma (n = 7) | 0% | 86% | 86% | 0% |
| Tubular adenoma (n = 6) | 0% | 83% | 100% | 17% |
| Juvenile polyps (n = 1) | 0% | 0% | 0% | 0% |

CC2 was not seen in any of the pre-malignant polyps. CC5 was present in only two (33%) pre-malignant TVA with HGD and in one (17%) TA. CC3 and CC4 were present in 83%–100% in TA, in 86% in TVA and in 83%–100% in TVA with HGD. None of the nuclear matrix proteins were seen in the juvenile polyp, which is not a precursor of colon cancer.

CC5, which was present in only 2 pre-malignant TVA with HGD and in one TA, but was present in all colon cancer tissues, is expressed at the junction of an advanced adenoma and invasive colon cancer. CC5 is a promising marker for malignant potential of colon polyps because it is expressed in the advanced polyps and in the colon cancer epithelia. CC3 and CC4 were present in most adenomas, regardless of advancement. Both proteins are expressed earlier in the development of adenomatous polyps and are also expressed in all colon cancer (Table: 2). The combination of all four CC markers tested also provides diagnostic value for early detection of malignant progression in colon polyps.

Example 3

Partial Amino Acid Sequence of Colon Carcinoma NMPs

A. Method for Polypeptide Isolation and Sequencing

A partial amino acid sequence was determined for particular CC markers isolated two-dimensional gels using an adaptation of a technique developed by Gevaert et al. (35). Briefly, two-dimensional gels run with NMP preparations were negatively stained by incubating in 0.2M Imidazole for 15 minutes, washing several times with deionized water, staining with a warmed solution of 0.3M zinc chloride and terminating the staining reaction by washing in deionized water. Protein spots were excised from the gel and frozen at −80° C. The gel spots were thawed, pooled and stained for 20 min with 0.25% Coomassie blue in 45% methanol/9% acetic acid. The isolated gel spots were destained by agitation in destaining solution (5% methanol/7.5% acetic acid) for 1 hour, washed with deionized water for 1 hour, and equilibrated in SDS polyacrylamide sample buffer (1% SDS/10% glycerol/50 mM DTT/12 mM Tris-HCl pH 7.1) for 1 hour before loading into an SDS acrylamide/agarose gel.

Following destaining, the protein from each gel spots was concentrated on a mini-agarose/acrylamide gel. The gel was formed between two pre-warmed (60° C.) glass plates (10 cm×9 cm), separated by spacers 1 cm wide and 1.5 mm thick. A strip of Whatman 3 MM paper was applied to the bottom to serve as a support for the lower agarose gel, preventing the gel from slippage during electrophoresis. A 2 cm wide×1.5 cm thick spacer was inserted between the two parallel spacers to form a sample well for receiving the gel spots. The sample well was formed by a 2 cm wide×1.5 cm thick spacer set between two parallel spacers each 1 cm wide×1.5 cm thick inserted at the center of the glass plates and attached with adhesive tape at the top edge of the back plate.

The running gel portion of the mini-gel consisted of a 2 cm deep agarose (1.45% agarose in 0.36 M Tris-HCl pH 8.7/0.1% SDS) which was poured and allowed to set. A polyacrylamide stacking gel (5.45% acrylamide/0.13% bisacrylamide/0.12 M Tris-HCl pH 6.8/0.1% SDS) was applied over the agarose. After the stacking gel polymerized, the central well-forming spacer was removed, leaving a loading well with dimensions 2 cm high, 2 cm wide and 1.5 mm thick. The mini concentration gel was then mounted on a small electrophoresis tank (BioRad, Hercules, Calif.), and the loading slot filled with the SDS sample buffer-equilibrated gel spots. The remaining volume was filled with blank gel pieces.

Mini-gels were run at 100 V, allowing the proteins to elute out of the combined gel pieces and into the acrylamide. At this time, the central spacer was re-inserted into the sample well until the dye front passed the two parallel 1 cm wide spacers. At that point, the central spacer was removed and electrophoresis continued until the dye front entered the agarose and reached the filter paper.

The agarose running gel was removed and fixed in fresh 50% methanol/10% acetic acid shaking, at room temperature for 30 minutes. The gel was stained with 0.05% Coomassie blue stain (50% methanol/10% acetic acid) for 5 minutes and then destained in 5% methanol/7% acetic acid for 2 hours with constant agitation. The protein band was then excised in a minimal volume of agarose gel, transferred to a sterile tube, and digested thoroughly with trypsin. Trypsin fragments were subjected to preparative reverse phase C18 HPLC and fractions containing different peptides were isolated. An automated sequencer was used to determine a sequence of fragments in different fractions.

B. Peptide Sequencing Results

N-terminal amino acid sequences for trypsin fragments of particular isolated CC polypeptides isolated from NMP preparations of Caco-2 cells is shown is Table 5 while the sequences for particular CC polypeptides isolated from NMP preparations of human colorectal cancer specimens are shown in Table 6.

TABLE 5

Partial Amino Acid Sequence of CC3 and CC6 Proteins Isolated from Caco-2 NMP Preparation

| Marker No. | Amino Acid Sequence (5'–3') | |
|---|---|---|
| CC6a | PXVKFNSYVDGVEV (peak 31) | (SEQ ID NO: 1) |
| | EGDLIEDY (peak 17) | (SEQ ID NO: 2) |
| CC3 | YPVEAFN (Peak 9) | (SEQ ID NO: 3) |
| | TVAPLFIVIPN (Peak 35) | (SEQ ID NO: 4) |
| | XVTGLTQIETLFAAPGVD (Peak 47) | (SEQ ID NO: 5) |
| | SMTEAEQQQLIDDHFLFDKPVSP (Peak 52) | (SEQ ID NO: 6) |
| | SLPQNIPPLTQTPV (Peak No: 31) | (SEQ ID NO: 7) |
| | VLPGEIVEYSR (Peak No: 15) | (SEQ ID NO: 8) |

TABLE 6

Partial Amino Acid Sequence of CC Proteins Isolated from Human Colorectal Tissue NMP Preparations

| Marker No. | Amino Acid Sequence (5'–3') | |
|---|---|---|
| CC1 | YTIFDNFLITNDEAYAEEFG (Peak 30) | (SEQ ID NO: 9) |
| | QIDNPDYKGTXIHPE (Peak 34) | (SEQ ID NO: 10) |
| | PAVYFKEQFLDGDGW (Peak 24) | (SEQ ID NO: 11) |
| | TLIVRPDNTYEVK (Peak 18) | (SEQ ID NO: 12) |
| | YAVLITVLQDS (Peak 13) | (SEQ ID NO: 13) |
| | AKTDFATFLYT (Peak 28) | (SEQ ID NO: 22) |
| CC2 | NLPQE (Peak 07) | (SEQ ID NO: 14) |
| | TEPELQDKIHQ (Peak 18) | (SEQ ID NO: 15) |
| | TDAPSFSDIPNL (Peak No: 20) | (SEQ ID NO: 16) |
| | LKYENEVALR (Peak No: 20) | (SEQ ID NO: 23) |
| | XQKEDVPSE (Peak No: 02) | (SEQ ID NO: 17) |
| CC3 | VYOEPLVFR (Peak 31) | (SEQ ID NO: 24) |
| | RAPFQELYND (Peak 31) | (SEQ ID NO: 25) |
| | XFYQLDAYPSGAXY (Peak 35) | (SEQ ID NO: 26) |
| CC4 | VIEAFNR (Peak 17) | (SEQ ID NO: 27) |
| | ILLFDYFNR (Peak 28) | (SEQ ID NO: 28) |
| | VLVALEPLS (Peak 29) | (SEQ ID NO: 29) |
| CC6a | NAFNDGLK (Peak 12) | (SEQ ID NO: 18) |
| | YFDSFGDLSSASAIMGN (Peak 19) | (SEQ ID NO: 19) |
| | TYFSFHIDVSPGSAQVK (Peak 18) | (SEQ ID NO: 20) |
| CC6b | SLDEQEQTK (Peak 06) | (SEQ ID NO: 21) |

The amino acid sequences were run against public amino acid sequence databases to determine if they represent previously known proteins. The sequence of amino acids fragments generated from CC1 (SEQ ID NOS: 9, 10 and 11) were consistent with the protein calreticulin, while CC1 sequences with SEQ ID NO: 12 and 13 were consistent with a precursor of calreticulin. Calreticulin is an important multifunctional calcium-binding protein and is the major calcium binding protein found in the membranes of smooth muscle sarcoplasmic reticulum and non-muscle endoplasmic reticulum (ER). Calreticulin has an immunological function in the folding and peptide-loading of newly synthesized molecules of the major histocompatability complex (MHC) class I protein. A complete MHC class I molecule consists of a 3-domain alpha-chain and a smaller β2-microglobulin bound to a short peptide fragment. When the β2-microglobulin first binds to the alpha-chain, this partially folded heterodimer binds to a complex of proteins including calreticulin. Calreticulin's binding of the MHC molecule is regulated by glucose trimming of nascent N-linked oligosaccharides—the oligosaccharide moiety in the alpha1 domain and a residue within the alpha3 domain of the MHC class I molecule are critical for intersection with calreticulin. After peptide loading and deglucosylation of N-linked glycans, calreticulin dissociates from the heterodimer.

Example 4

Identification of Calreticulin in Colon Cancer NMP Preparations

The presence of calreticulin in colon cancer was evaluated using NMP preparations as well as nuclear and cytoplasmic extracts.

A. Methods

Nuclear and Cytoplasmic Extraction: NE-PER nuclear and cytoplasmic extraction reagents (Pierce Chemical Co., Rockford, Ill.) were used for the preparation of nuclear and cytoplasmic extracts. The protein concentration was quantitated by Coomassie Plus protein assay (Pierce Chemical Co., Rockford, Ill.) with bovine serum albumin as a standard.

One-Dimensional Immunoblot: One-dimensional immunoblot analysis was performed according to standard established protocols. Ten µg of each sample of extracted NMPs was suspend in PBS (phosphatase buffered salt solution) and nuclear and cytoplasmic extracts suspend in nuclear extraction reagent (NER) or in cytoplasmic extraction reagent (CERII) were separated by 12% SDS-PAGE. Ten µl of Rainbow markers (Amersham Life Sciences, Arlington Heights, Ill.) were also loaded. Proteins were then transferred to a polyvinylidene difluoride membrane (Millipore, Bedford, Mass.), and the membrane was blocked overnight in 4% nonfat dry milk in PBS with 0.2% Tween® 20 at 4° C. The membrane was then washed with PBS and 0.2% Tween® 20, followed by a 1-h incubation with a 1:2000 dilution of anti-calreticulin IgG (Research Diagnostics, N.C., Flanders, N.J.) and 2% nonfat dry milk with 0.2% Tween® 20 in PBS. The membrane was further washed with PBS and 0.2% Tween® 20 and incubated for 1 h in a 1:5000 dilution of goat anti-rabbit IgG (Amersham Life Sciences, Arlington Heights, Ill.) secondary antibody conjugated with horseradish peroxidase (Amersham Life Sciences, Arlington Heights, Ill.). For determination of the relative purity of each protein extraction, the membranes were probed with a monoclonal α-tubulin mouse antibody (1:500) (specific for cytoplasmic tubulin) and 2% nonfat dry milk with 0.2% Tween® 20 in PBS. These membranes were further washed with PBS and 0.2% Tween®20 and incubated for 1 hour in a 1:5000 dilution of goat anti-mouse IgG (Amersham Life Sciences, Arlington Heights, Ill.) conjugated with horseradish peroxidase. The membranes were washed again with PBS and 0.2% Tween® 20 and the proteins detected by chemiluminescence reaction using the ECL immunoblot kit (Amersham Life Sciences, Arlington Heights, Ill.).

Two-dimensional immunoblot: After performing 2-D electrophoresis, the area of the gel where the spot was located and which the peptide sequence resulted in identification as calreticulin was removed and was transferred to a polyvinylidene difluoride membrane (Millipore, Bedford, Mass.). This area of the gel was utilized instead of the entire gel, because the large gel format makes blotting and processing difficult. Thereafter, the same procedure described above for the one-dimensional immunoblot was followed by a 1-h incubation with a 1:2000 dilution of anti-calreticulin IgG (Research Diagnostics, Inc., Flanders, N.J.) with 2% nonfat dry milk with 0.2% Tween® 20 in PBS. The membrane was further washed with PBS and 0.2% Tween® 20 and incubated for 1 h in a 1:5000 dilution of goat anti-rabbit IgG (Amersham Life Sciences, Arlington Heights, Ill.) secondary antibody conjugated with horseradish peroxidase (Amersham Life Sciences, Arlington Heights, Ill.). The membrane was washed again with PBS and 0.2% Tween® 20 and proteins were detected by a chemiluminescence reaction using the ECL immunoblot kit (Amersham Life Sciences, Arlington Heights, Ill.).

B. Results

The two-dimensional immunoblot of CC1 probed positive with the anti-calreticulin antibody. A one-dimensional immunoblot of colon cancer, normal adjacent and normal donor colon tissue cytoplasmic, nuclear and nuclear matrix protein fractions was probed with antibodies specific for calreticulin and α-tubulin (cytoplasmic 51 kD protein). Tubulin was not detectable in nuclear and the nuclear matrix protein fractions indicating the that lack of contamination of cytoplasmic material in these fractions. Calreticulin was detected (about a 60 kD band) in human colon cancer tissue, adjacent normal tissue and normal donor tissue in all three different protein fractions. These results show that calreticulin is present in the nuclear protein fraction and more specifically in the nuclear matrix protein fraction of colon cancer cells, and that such presence is not due to contamination by cytoplasmic calreticulin. Calreticulin was less detectable in normal adjacent and normal donor colon tissue NMP preparations by one dimensional inmunoblotting.

Example 5

Identification of NMPs Characteristic of Liver Metastases and Primary Colon Cancer Cells A. Expression of L1–L5 Proteins in NMPs from Various Sources High-resolution two-dimensional gel electrophoresis of various NMP preparations identified five proteins (L1–L5) of clinical value (Table 7). NMPs L1–L5 were detectable in about 83% to 100% of 2D gels for NMP preparations of the various colon cancer to liver metastases. L1–L5 were undetectable in NMP preparations of normal hepatocytes. Three proteins, L1, L2 and L5, were undetectable in NMP preparations of normal donor liver tissue, and two proteins, L3 and L4, were detectable in a lower percentage of gels prepared from NMP preparations of normal donor liver tissue as compared to that of colon to liver metastasis. Four of the proteins (L1, L2, L4 and L5) were detectable in less than 40% in the adjacent normal liver tissue samples (Table 7), while protein L3 was detectable in 92% of the adjacent liver tissue samples (Table 7).

Proteins L1, L2, L3 and L4 also were detectable in 60% or more of gels prepared using NMP preparations of primary colon cancer cells (Table 7). Protein L5, on the other hand, was detectable in only 20% of gels prepared using NMP preparations of in primary colon cancer cells (Table 7). Proteins L3 and L4 were expressed in 100% of gels prepared using NMP preparations of the normal adjacent colon and 100% and 75% respectively for donor colon tissue. Protein L2 was expressed in 10% of the adjacent normal colon tissue, while L1 was not detectable in the adjacent normal colon, but was detectable in one of the four donor colon samples (25% in Table 7). Electrophoretic characteristics of the identified proteins are shown in Table 7.

Thus, L1–L5 are differentially expressed in normal liver metastases versus normal hepatocytes. L2 and L2 are the most differential of all proteins, the difference being seen in both colon liver metastases versus adjacent liver tissue and in primary colon cancer versus adjacent colon tissue. L3 is differential for liver metastases versus adjacent liver tissue or for primary colon cancer versus normal adjacent colon.

TABLE 7

Characteristics of NMPs in Liver Metastases and Other Liver and Colon Tissues

| | | | 2D Gel Tissue Expression | | | | | | |
|---|---|---|---|---|---|---|---|---|---|
| Markers/ NMPs | Mr. (kD) | PI | Colon Ca. to Liver mets. (n = 12) | Normal Adj. liver (n = 12) | Normal donor liver (n = 3) | Normal Hepatocytes | Colon Ca. (n = 10) | Normal Adj. Colon (n = 10) | Normal donor colon (n = 4) |
| $L_1$ | 50 | 6.01 | 92% | 42% | 0% | 0% | 70% | 0% | 25 |
| $L_2$ | 20 | 5.73 | 100% | 17% | 0% | 0% | 100% | 10% | 0% |
| $L_3$ | 17 | 6.09 | 100% | 92% | 33% | 0% | 90% | 100% | 100 |
| $L_4$ | 17 | 6.00 | 100% | 17% | 33% | 0% | 60% | 100% | 75% |
| $L_5$ | 18 | 5.88 | 83% | 8% | 0% | 0% | 20% | 0% | 0% |

Adj. = adjacent;
Ca—cancer;
mets = metastasis

B. Analysis of NMPs from Liver and Colon Cancer Tissue and Cell Lines

Tissue samples are complex mixtures of epithelial, stromal, immunological and other cell types. To determine whether the nuclear matrix changes detected actually represented changes that were occurring in the neoplastic cells, as well as to identify potential models, the NMP composition of two human primary liver cancer cell lines were examined. While the NMP fingerprints from the pure cell lines would be expected to be distinct from the three dimensional complex of liver metastasis and colon cancer specimens they serve as tools for generating reagents as well as examining a single cell type. The human liver cancer cell lines Huh 7 and HepG 2 and the human colon cancer cell lines Caco-2 and SW480 were grown and their NMPs were isolated. These NMPs were then separated and analyzed as described above. The cell line HepG 2 expressed none of the liver metastasis associated proteins, and the Huh 7 cell line expressed one of the liver metastasis associated proteins (L1). The cell line Caco-2 expressed two of the proteins (L3, L2) and the cell line SW480 expressed just one protein (L2). Electrophoretic characteristics of the identified proteins in these cell lines are shown in Table 8.

TABLE 8

Characteristics of NMPs in Colon Cancer Cell Lines

| Markers/ NMPs | Mr. (kD) | PI | 2D-Gel Cell Expression | | | |
|---|---|---|---|---|---|---|
| | | | Hep $G_2$ | Huh 7 | Caco-2 | SW 480 |
| $L_1$ | 50 | 6.01 | 0% | 0% | 0% | 0% |
| $L_2$ | 20 | 5.73 | 0% | 0% | 100% | 100% |
| $L_3$ | 17 | 6.09 | 0% | 0% | 100% | 0% |
| $L_4$ | 17 | 6.00 | 0% | 0% | 0% | 0% |
| $L_5$ | 19 | 5.88 | 0% | 0% | 0% | 0% |

These studies demonstrate that nuclear matrix proteins uniformly present in NMP preparations from human liver metastasis are not readily present in NMP preparations of normal donor tissue or isolated hepatocytes. In addition, in some cases, the normal adjacent liver tissue contains alterations in the nuclear matrix pattern similar to those found in liver metastasis. These five proteins were also found to varying degrees in primary colon cancer, but were not found in other cancer types.

The functional identification of these proteins and their detection through the generation of NMP antibodies could be used to develop tests for colon cancer prognosis and early detection of metastases. Antibodies are generated to detect specific nuclear matrix proteins in the blood or tissue samples. Assay is developed that include the detection and combination of individuals proteins identified herewith. Development of assays with these antibodies potentially serve as tumor marker with high sensitivity and specificity.

Additionally the presence of unique NMPs in liver metastasis or the up regulation in cancer cells could provide novel information about their function in development of metastasis and provide us with additional targets for anticancer therapies.

Example 6

Isolation of "L" Proteins from 2-D Gels and Sequencing

Methods for isolating and sequencing L proteins were as described for the CC proteins in Example 3. N-terminal amino acid sequences for trypsin fragments of particular isolated L polypeptides isolated from NMP preparations of colorectal metastases to liver cells is shown is Table 9.

TABLE 9

Partial Amino Acid Sequence of L2 and L5 Proteins Isolated from Human Colorectal Metastases to Liver NMP Preparations

| Marker No. | Amino Acid Sequence (5'-3') | |
|---|---|---|
| L2 | QFYQLDAYPSGAWYYVP (Peak *) | (SEQ ID NO: 30) |
| | FFVALFPEVF (Peak 23) | (SEQ ID NO: 31) |
| | QFYQLDAYPSGAWYYVP (Peak 31) | (SEQ ID NO: 32) |
| L5 | TDAPSFSDIPNL (Peak No: 20) | (SEQ ID NO: 33) |
| | FFVALFPEVFGK (Peak No: 26) | (SEQ ID NO: 34) |
| | QFYQL (Peak No: 28) | (SEQ ID NO: 35) |
| | AVPYPQRDMPI (Peak 38) | (SEQ ID NO: 36) |

PUBLICATION LIST

1. Wu et al., *Dis. Colon Rectum*, 43: 1473–1486, 2000.
2. Greenlee et al., *CA Cancer J. Clin.*, 50: 7–33, 2000.
3. Ahlquist, *Gastroenterol. Clin. North Am.*, 26: 41–55, 1997.
4. Silvis et al., *JAMA*, 235: 928–930, 1976.
5. Geenen et al., *Am. J. Dig. Dis.*, 20: 231–235, 1975.
6. Goldenberg et al., *J. Natl. Cancer Inst.*, 57: 11–22, 1976.
7. Carriquiry et al., *Dis. Colon Rectum*, 42: 921–929, 1999.
8. Wanebo et al., *New. Engl. J. Med.*, 299: 448–451, 1978.
9. Martell et al., *Int. J. Biol. Markers*, 13: 145–149, 1998.
10. Moertel et al., *JAMA*, 270: 943–947, 1993.
11. Herrera et al., *Ann. Surg.*, 183: 5–9, 1976.
12. Reynoso et al., *JAMA*, 220: 361–365, 1972.
13. Merrifield, *J. Am. Chem. Soc.* 85: 2149 (1962).
14. Stewart and Young, SOLID PHASE PEPTIDE SYNTHESIS, 27–62 (Freeman Publ., 1969).
15. Kabat et al., SEQUENCES OF PROTEINS OF IMMUNOLOGICAL INTEREST 4th ed., U.S. Dept. Health and Human Services, Public Health Services (Bethesda, Md., 1987).
16. Huston et al., *Proc. Nat'l Acad. Sci. USA*, 85:5879–5883, 1988.
17. Harlow et al., ANTIBODIES: A LABORATORY MANUAL (Cold Spring Harbor Laboratory, 1988).
18. Goeddel et al., *Meth. Enzymol.*, 185: 3–7 (Academic Press, NY, 1990).
19. Uhlen & Moks, *Meth. Enzymol.*, 185: 129–143 (Academic Press, NY, 1990)
20. Hermanson, *Bioconjugate Techniques*, Academic Press, San Diego, Calif. (1996).
21. Wray et al., *Anal. Biochem.*, 118: 197–203, 1981.
22. Godreau, *Fam. Pract. Res. J.*, 12: 313–320, 1992.
23. Berezney et al.,. *Biochem. Biophys. Res. Commun.*, 60: 1410–1417, 1974.
24. Fey et al., *Crit Rev. Eukaryot. Gene Expr.*, 1: 127–143, 1991.
25. Getzenberg, et al., *Endocrine Reviews*, 11: 399–417, 1990.
26. Getzenberg, *Journal of Cellular Biochemistry*, 55: 22–31, 1994.
27. Konety et al., *Journal of Urology*, 159: 1359–1363, 1998.
28. Getzenberg et al., *Cancer Res*, 56: 1690–1694, 1996.
29. Getzenberg et al., *Cancer Res*, 51: 6514–6520, 1991.
30. Brunagel et al., *Cancer. Cancer Res*, 62: 2437–2442, 2002.
31. Miller et al., *Cancer Res.*, 52: 422–427, 1992.
32. Keesee et al., *Proc. Natl. Acad. Sci. U.S.A*, 91: 1913–1916, 1994.
33. Patton et al., *Biotechniques*, 8: 518–527, 1990.
34. Boyd et al., *Journal of the National Cancer Institute*, 83: 862–866, 1991.
35. Gevaert et al., in METHODS IN PROTEINS STRUCTURE ANALYSIS, Plenum Press, New York (1995).

The invention thus has been disclosed broadly and illustrated in reference to representative embodiments described above. Those skilled in the art will recognize that various modifications can be made to the present invention without departing from the spirit and scope thereof.

What is claimed is:

1. A monoclonal antibody which binds to a peptide consisting of SEQ ID NO: 28.

* * * * *